United States Patent [19]

Arahira et al.

[11] Patent Number: 5,292,764
[45] Date of Patent: Mar. 8, 1994

[54] AZOLE DERIVATIVES FOR PROTECTING INDUSTRIAL MATERIALS FROM BACTERIA

[75] Inventors: Masato Arahira; Toshihide Saishoji, both of Iwaki; Katsuhisa Ohsugi, Tokyo; Satoru Kumazawa, Iwaki, all of Japan

[73] Assignee: Kureha Kagaku Kogyo K.K., Tokyo, Japan

[21] Appl. No.: 918,152

[22] Filed: Jul. 24, 1992

Related U.S. Application Data

[63] Continuation of Ser. No. 604,397, Oct. 26, 1990, abandoned, which is a continuation of Ser. No. 344,932, Apr. 28, 1989, abandoned.

[30] Foreign Application Priority Data

May 10, 1988 [JP] Japan .................. 63-111713
Aug. 12, 1988 [JP] Japan .................. 63-200051

[51] Int. Cl.$^5$ .................. A61K 31/41; A61K 31/415
[52] U.S. Cl. .................. 514/383; 514/399
[58] Field of Search .................. 514/383, 399

[56] References Cited

U.S. PATENT DOCUMENTS

| | | | |
|---|---|---|---|
| 4,329,342 | 5/1982 | Heeres | 424/245 |
| 4,503,062 | 3/1985 | Gravestock | 514/383 |
| 4,670,454 | 6/1987 | Janssen | 514/383 |
| 4,684,396 | 8/1987 | Clough et al. | 514/383 |
| 4,806,565 | 2/1991 | Hensens | 514/467 |

FOREIGN PATENT DOCUMENTS

| | | |
|---|---|---|
| 0267778 | 5/1988 | European Pat. Off. . |
| 267778 | 5/1988 | European Pat. Off. . |
| 605488 | 5/1987 | Japan . |
| 62-149667 | 7/1987 | Japan . |
| 7822 | 4/1988 | Japan . |
| 1-93574 | 4/1989 | Japan . |
| 2180236A | 3/1987 | United Kingdom . |

OTHER PUBLICATIONS

CA 109:93024t, Sep. 1988.
CA 106:213957m, Jun. 1987.

*Primary Examiner*—Frederick E. Waddell
*Assistant Examiner*—Gregory Hook
*Attorney, Agent, or Firm*—Lowe, Price, LeBlanc & Becker

[57] ABSTRACT

Disclosed herein is a method for preventing deterioration of an industrial material by using an azole derivative represented by the following formula

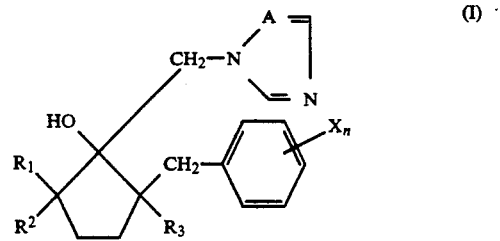

wherein X means a halogen atom or a $C_1-C_5$ alkyl, haloalkyl, phenyl, cyano or nitro group, n stands for 0 or an integer of 1-5, A denotes a nitrogen atom or CH, $R_1$ and $R_2$ mean individually a hydrogen atom or a $C_1-C_5$ alkyl group, $R_3$ denotes a hydrogen atom or a $C_1-C_3$ alkyl group, and when n is an integer of 2-5, Xs may be the same or different. A biocidal composition for the method is also disclosed.

6 Claims, No Drawings

AZOLE DERIVATIVES FOR PROTECTING INDUSTRIAL MATERIALS FROM BACTERIA

This application is a continuation of application Ser. No. 07/604,397 filed Oct. 26, 1990, now abandoned which is a continuation of application Ser. No. 07/344,932 filed Apr. 28, 1989, now abandoned.

BACKGROUND OF THE INVENTION

1. Field of the Invention

This invention relates to biocidal compositions for industrial materials. It also pertains to a method for preventing deterioration of industrial materials.

2. Description of the Related Art

It has already been disclosed by the present inventors in GB 2180236 A that the compounds represented by the following formula (A) have plant disease controlling effects, plant growth controlling effects and herbicidal effects and can hence be used as agricultural and horticultural chemicals.

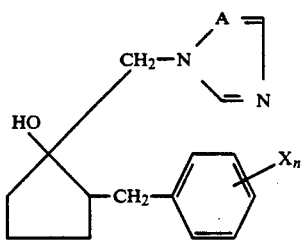

(A)

wherein X means a halogen atom or a $C_1$-$C_5$ alkyl, haloalkyl, phenyl, cyano or nitro group, n stands for 0 or an integer of 1-5, A denotes a nitrogen atom or CH, and when n is an integer of 2-5, Xs may be the same or different.

The present inventors also studied a group of azole derivatives including the compounds represented by the formula (A). As a result, it was found that in addition to the compounds represented by the formula (A), such azole derivatives also include those useful as agricultural and horticultural chemicals and further those not only capable of acting as an agricultural and horticultural chemical but also having effective antifungal activities in animals including human being [Japanese Patent Application Nos. 317754/1987 (corresponding to U.S. patent application Ser. No. 201982 of Jun. 3, 1988), 6054/1988 and 7822/1988].

By the way, industrial materials, for example, natural materials such as paper, fibers, lumber and leather, synthetic materials such as paints and plastic materials, metal materials, inorganic materials and products formed of such materials are often contaminated by noxious microorganisms and deteriorated in quality. There has hence been a strong demand for the development of chemicals effective against microorganisms noxious to these industrial materials.

The present inventors have proceeded with a further investigation on the utility of the azole derivatives mentioned above. As a result, it has been found that a certain groups of azole derivatives have strong activities against microorganisms noxious to such industrial materials as referred to above, said microorganisms being totally different in field from microorganisms causing disease on agricultural and horticultural crops or fungi causing disease on human being and animals, leading to completion of this invention.

SUMMARY OF THE INVENTION

An object of this invention is therefore to provide a biocidal composition effective against microorganisms which are noxious to industrial materials.

Another object of this invention is to provide a method for preventing deterioration of industrial materials.

In one aspect of this invention, there is thus provided a biocidal composition for an industrial material, comprising as an effective ingredient an azole derivative represented by the following formula (I):

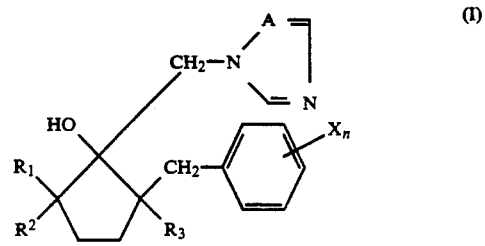

(I)

wherein X means a halogen atom or a $C_1$-$C_5$ alkyl, haloalkyl, phenyl, cyano or nitro group, n stands for 0 or an integer of 1-5, A denotes a nitrogen atom or CH, $R_1$ and $R_2$ mean individually a hydrogen atom or a $C_1$-$C_5$ alkyl group, $R_3$ denotes a hydrogen atom or a $C_1$-$C_3$ alkyl group, and when n is an integer of 2-5, Xs may be the same or different.

In another aspect of this invention, there is also provided a method for preventing deterioration of an industrial material, which comprises applying to the industrial material, which comprises applying to the industrial material a biocidally-effective amount of the azole derivative represented by the formula (I).

In the present invention, the azole derivative represented by the formula (I) has as its structural feature an azolylmethyl group at the 1-position of the cyclopentane ring, a substituted benzyl group or both a substituted benzyl group and a $C_1$-$C_3$ alkyl group at the 2-position, and a hydrogen atom or $C_1$-$C_5$ alkyl group at the 5-position. The above azole derivative useful in the practice of this invention therefore includes stereoisomers such as geometric isomers, i.e., cis-isomer and transisomer and optical isomers. This invention embraces not only single use of these isomers but also the use of mixtures containing individual isomers at desired ratios. In other words, it should be noted that the bicoidal composition according to this invention contains these isomers either singly or in combination as active ingredient or ingredients. Since the above azole derivative contains a 1,2,4-triazole ring or imidazole ring, the azole derivative can be used in a form such as an acid addition salt with an inorganic acid or organic acid, a metal complex or the like.

As will become apparent from results of tests to be described subsequently, the compound represented by the formula (I) exhibits strong activities against noxious microorganisms which contaminate industrial materials and cause their quality deterioration. When the biocidal composition according to this invention is applied, for example, to a natural material such as paper, fibers, lumber or leather, a synthetic material such as a paint coating, rubber or synthetic resin, a metallic material, inorganic material, or a product formed of the above-mentioned material, it can effectively prevent contamination or quality deterioration of such an industrial material.

DETAILED DESCRIPTION OF PREFERRED EMBODIMENTS

As illustrative examples of the azole derivative represented by the formula (I) and useful in the practice of this invention, may be mentioned compounds shown below in Table 1, in which the designated types of stereoisomers, namely, A type and B type mean those having the following structures respectively.

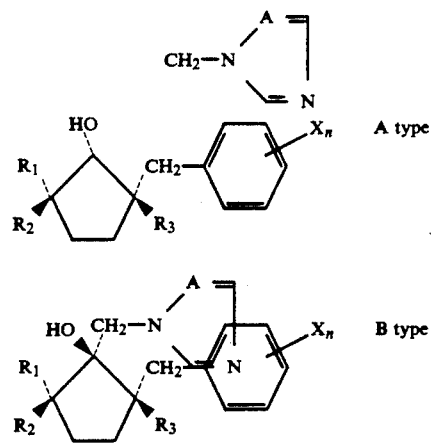

---: extending below the plane of the page
—: extending on the plane of the page
▶: extending above the plane of the page

TABLE 1

| Compound No. | Variables in formula (I) | | | | | Type of stereoisomer | Melting point (°C.) |
|---|---|---|---|---|---|---|---|
| | $R_1$ | $R_2$ | $R_3$ | Xn | A | | |
| 1 | $CH_3$ | $CH_3$ | H | 4-Cl | N | A | 113–114 |
| 2 | $CH_3$ | $CH_3$ | H | 4-Cl | N | B | 113–114 |
| 3 | $CH_3$ | $CH_3$ | H | 4-Cl | CH | A | 133–134 |
| 4 | $CH_3$ | $CH_3$ | H | 4-Cl | CH | B | 133–134 |
| 5 | $CH_3$ | $CH_3$ | H | 4-Br | N | A | 129–130 |
| 6 | $CH_3$ | $CH_3$ | H | 4-Br | N | B | 134–135 |
| 7 | $CH_3$ | $CH_3$ | H | 4-Br | CH | A | 149–150 |
| 8 | $CH_3$ | $CH_3$ | H | 4-Br | CH | B | 134–135 |
| 9 | $CH_3$ | $CH_3$ | H | 4-F | N | A | 135–136 |
| 10 | $CH_3$ | $CH_3$ | H | 4-F | N | B | 134–135 |
| 11 | $CH_3$ | $CH_3$ | H | 4-F | CH | A | 131–133 |
| 12 | $CH_3$ | $CH_3$ | H | 4-F | CH | B | 104–106 |
| 13 | $CH_3$ | $CH_3$ | H | 2,4-$Cl_2$ | N | A | 126–127 |
| 14 | $CH_3$ | $CH_3$ | H | 2,4-$Cl_2$ | N | B | 108–110 |
| 15 | $CH_3$ | $CH_3$ | H | 2,4-$Cl_2$ | CH | A | 131–132 |
| 16 | $CH_3$ | H | H | 4-Cl | N | A | 100–102 |
| 17 | $CH_3$ | H | H | 4-Cl | CH | A | 118–119 |
| 18 | H | $CH_3$ | H | 4-Cl | N | A | 75–76 |
| 19 | H | $CH_3$ | H | 4-Cl | N | B | 79–81 |
| 20 | $CH_3$ | H | H | 4-Cl | N | B | oily substance |
| 21 | $CH_3$ | $CH_3$ | H | H | N | A | oily substance |
| 22 | $CH_3$ | $CH_3$ | H | H | CH | A | 128–130 |
| 23 | $CH_3$ | $CH_3$ | H | 4-$CH_3$ | N | A | 123–124 |
| 24 | $CH_3$ | $CH_3$ | H | 4-$CH_3$ | N | B | 114–115 |
| 25 | $CH_3$ | $CH_3$ | H | 4-$CH_3$ | CH | A | 132–133 |
| 26 | $CH_3$ | $CH_3$ | H | 4-$CH_3$ | CH | B | 130–131 |
| 27 | $CH_3$ | $CH_3$ | H | 2-F, 4-Cl | N | A | 129–130 |
| 28 | $CH_3$ | $CH_3$ | H | 2-F, 4-Cl | CH | A | 152–154 |
| 29 | $C_2H_5$ | H | H | 4-Cl | N | A | 82–84 |
| 30 | H | $C_2H_5$ | H | 4-Cl | N | A | 93–95 |
| 31 | H | $C_2H_5$ | H | 4-Cl | N | B | 76–78 |
| 32 | $C_2H_5$ | H | H | 4-Cl | N | B | 110–112 |
| 33 | $C_2H_5$ | $C_2H_5$ | H | 4-Cl | N | A | 124–126 |
| 34 | $C_2H_5$ | $C_2H_5$ | H | 4-Cl | N | B | 143–145 |
| 35 | $C_2H_5$ | $C_2H_5$ | H | 4-Cl | CH | A | oily substance |
| 36 | $C_2H_5$ | $C_2H_5$ | H | 4-Cl | CH | B | 143–145 |
| 37 | n-$C_3H_7$ | H | H | 4-Cl | N | A | 83–85 |
| 38 | H | n-$C_3H_7$ | H | 4-Cl | N | A | 75–77 |
| 39 | n-$C_3H_7$ | H | H | 4-Cl | CH | A | 115–117 |
| 40 | $C_2H_5$ | H | H | 2,4-$Cl_2$ | N | A | 124–127 |
| 41 | $C_2H_5$ | H | H | 2,4-$Cl_2$ | CH | A | 111–113 |
| 42 | $C_2H_5$ | H | H | 4-F | N | A | 73–74 |
| 43 | $C_2H_5$ | H | H | 4-F | CH | A | 111–113 |
| 44 | $C_2H_5$ | H | H | 4-Br | N | A | 80–82 |
| 45 | $C_2H_5$ | H | H | 4-Br | CH | A | 117–119 |
| 46 | $C_2H_5$ | H | H | 4-$C_6H_5$ | N | A | 107–109 |

TABLE 1-continued

| Compound No. | Variables in formula (I) | | | | | Type of stereoisomer | Melting point (°C.) |
|---|---|---|---|---|---|---|---|
| | $R_1$ | $R_2$ | $R_3$ | Xn | A | | |
| 47 | $C_2H_5$ | H | H | 4-$C_6H_5$ | CH | A | 169–170 |
| 48 | $C_2H_5$ | H | H | 4-t-$C_4H_9$ | N | A | oily substance |
| 49 | $C_2H_5$ | H | H | 4-t-$C_4H_9$ | CH | A | 132–133 |
| 50 | i-$C_3H_7$ | H | H | 4-Cl | N | A | 91–92 |
| 51 | n-$C_5H_{11}$ | H | H | 4-Cl | N | A | oily substance |
| 52 | n-$C_5H_{11}$ | H | H | 4-Cl | CH | A | 92–95 |
| 53 | $C_2H_5$ | H | H | 4-Cl | CH | B | 138–140 |
| 54 | H | n-$C_5H_{11}$ | H | 4-Cl | N | A | oily substance |
| 55 | $CH_3$ | $CH_3$ | H | 4-$C_6H_5$ | N | A | 122–124 |
| 56 | $CH_3$ | $CH_3$ | H | 4-$C_6H_5$ | N | B | 116–118 |
| 57 | $CH_3$ | $CH_3$ | H | 4-$C_6H_5$ | CH | A | 162–163 |
| 58 | $CH_3$ | $CH_3$ | H | 4-$C_6H_5$ | CH | B | 165–167 |
| 59 | i-$C_3H_7$ | H | H | 4-Cl | CH | A | oily substance |
| 60 | $CH_3$ | $CH_3$ | H | 4-t-$C_4H_9$ | N | A | 107–108 |
| 61 | $CH_3$ | $CH_3$ | H | 4-t-$C_4H_9$ | CH | A | 167–168 |
| 62 | H | i-$C_3H_7$ | H | 4-Cl | N | B | oily substance |
| 63 | H | i-$C_3H_7$ | H | 4-Cl | N | A | 102–103 |
| 64 | H | i-$C_3H_7$ | H | 4-Cl | CH | A | 146–147 |
| 65 | i-$C_3H_7$ | H | H | 4-Cl | N | B | 120–121 |
| 66 | n-$C_4H_9$ | H | H | 4-Cl | CH | A | oily substance |
| 67 | H | n-$C_4H_9$ | H | 4-Cl | N | A | 94–95 |
| 68 | H | n-$C_4H_9$ | H | 4-Cl | N | B | oily substance |
| 69 | i-$C_4H_9$ | H | H | 4-Cl | N | A | oily substance |
| 70 | i-$C_4H_9$ | H | H | 4-Cl | CH | A | oily substance |
| 71 | n-$C_4H_9$ | H | H | 4-Cl | N | A | oily substance |
| 72 Isomer a | $CH_3$ | $C_2H_5$ | H | 4-Cl | N | A | 72-a/72-b |
| Isomer b | $C_2H_5$ | $CH_3$ | H | 4-Cl | N | A | mixture 98–101 |
| 73 Isomer a | $CH_3$ | $C_2H_5$ | H | 4-Cl | N | B | 73-a/73-b |
| Isomer b | $C_2H_5$ | $CH_3$ | H | 4-Cl | N | B | mixture 117–119 |
| 74 Isomer a | $CH_3$ | $C_2H_5$ | H | 4-Cl | CH | B | 74-a/74-b |
| Isomer b | $C_2H_5$ | $CH_3$ | H | 4-Cl | CH | B | mixture 122–127 |
| 75 | $CH_3$ | $CH_3$ | H | 4-t-$C_4H_9$ | N | B | oily substance |
| 76 | $CH_3$ | $CH_3$ | H | 4-t-$C_4H_9$ | CH | B | 132–133 |
| 77 | H | H | H | H | N | A | 140–141 |
| 78 | H | H | H | H | CH | A | 130–131 |
| 79 | H | H | H | 4-$CH_3$ | N | A | 128–129 |
| 80 | H | H | H | 4-$CH_3$ | CH | A | 122–123 |
| 81 | H | H | H | 4-t-$C_4H_9$ | N | A | 129–130 |
| 82 | H | H | H | 4-t-$C_4H_9$ | CH | A | 123–124 |
| 83 | H | H | H | 2-Cl | N | A | 154–155 |
| 84 | H | H | H | 2-Cl | CH | A | 103–104 |
| 85 | H | H | H | 3-Cl | N | A | 152–153 |
| 86 | H | H | H | 3-Cl | CH | A | 105–106 |
| 87 | H | H | H | 4-Cl | N | A | 115–116 |
| 88 | H | H | H | 4-Cl | CH | A | 115–116 |
| 89 | H | H | H | 2,4-$Cl_2$ | N | A | 120–121 |
| 90 | H | H | H | 2,4-$Cl_2$ | CH | A | 150–151 |
| 91 | H | H | H | 4-F | N | A | 135–136 |
| 92 | H | H | H | 4-F | CH | A | 139–140 |
| 93 | H | H | H | 2,4-$F_2$ | N | A | 118–119 |
| 94 | H | H | H | 2,4-$F_2$ | CH | A | 144–145 |
| 95 | H | H | H | 2,6-$F_2$ | N | A | 104–105 |
| 96 | H | H | H | 2,6-$F_2$ | CH | A | 150–151 |
| 97 | H | H | H | 3,4-$F_2$ | N | A | 119–121 |
| 98 | H | H | H | 3,4-$F_2$ | CH | A | 103–105 |
| 99 | H | H | H | 2,3,4,5,6-$F_5$ | N | A | 118–120 |

TABLE 1-continued

| Compound No. | Variables in formula (I) | | | | | Type of stereoisomer | Melting point (°C.) |
|---|---|---|---|---|---|---|---|
| | $R_1$ | $R_2$ | $R_3$ | $X_n$ | A | | |
| 100 | H | H | H | 3-CF$_3$ | N | A | 152–153 |
| 101 | H | H | H | 3-CF$_3$ | CH | A | 87–88 |
| 102 | H | H | H | 2-F, 4-Cl | N | A | 125–127 |
| 103 | H | H | H | 2-F, 4-Cl | CH | A | 141–143 |
| 104 | H | H | H | 4-Br | N | A | 106–107 |
| 105 | H | H | H | 4-Br | CH | A | 119–120 |
| 106 | H | H | H | 4-C$_6$H$_5$ | N | A | 146–147 |
| 107 | H | H | H | 4-C$_6$H$_5$ | CH | A | 182–183 |
| 108 | H | H | H | 4-NO$_2$ | N | A | 131–132 |
| 109 | H | H | H | 4-CN | N | A | 115–116 |
| 110 | H | H | H | 4-CN | CH | A | 103–104 |
| 111 | CH$_3$ | CH$_3$ | CH$_3$ | 4-Cl | N | A | 159–160 |
| 112 | CH$_3$ | CH$_3$ | CH$_3$ | 4-Cl | N | B | 178–179 |
| 113 | CH$_3$ | CH$_3$ | CH$_3$ | 4-Cl | CH | A | 186–187 |
| 114 | CH$_3$ | CH$_3$ | CH$_3$ | 4-Cl | CH | B | 157–158 |

The azole derivatives useful in the practice of this invention can each be prepared by reacting an oxirane compound, which is represented by the following formula (II):

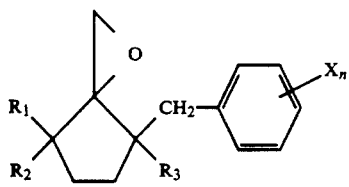
(II)

wherein X, $R_1$, $R_2$, $R_3$ and n have the same meanings as defined above, with a compound represented by the following formula (III):

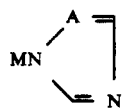
(III)

wherein M means a hydrogen atom or alkali metal and A has the same meaning as defined above, in the presence of a diluent.

Incidentally, the oxirane compound represented by the formula (II) can be obtained by reacting a cyclopentanone represented by formula (IV) below, for example, with dimethyloxosulfonium methylide or dimethylsulfonium methylide in the presence of a diluent, for example, in light of the process described in Organic Synthesis, 49, 78 (1968) and Journal of American Chemical Society, 1353 (1965).

Still more, as a different method, there is a method by which a methylenecyclopentane represented by the formula (V) is obtained from a cyclopentanone represented by the formula (IV) through the Witting reaction [refer to Org. Syn. 40, 66 (1966) and J. Org. Chem. 28, 1128 (1963)], and then the oxirane derivative represented by the formula (II) can be obtained from the thus prepared compound by the epoxidation [refer to Org. Syn. Coll. Vol., 4, 552 (1963) and Org. Syn., 49, 62 (1969)].

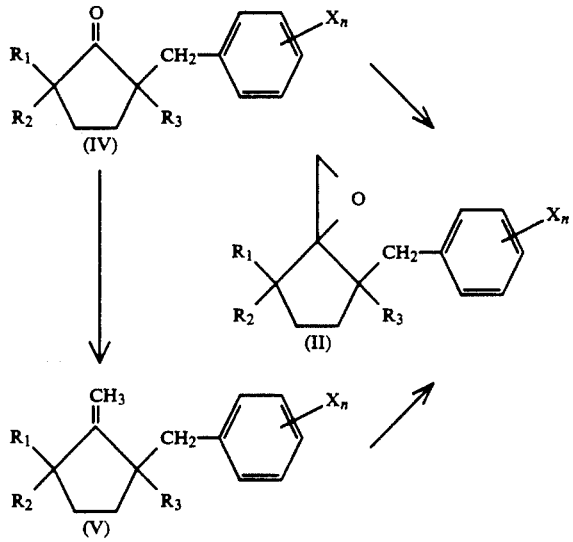

wherein X, $R_1$, $R_2$, $R_3$ and n have the same meanings as defined above.

The biocidal compositions for industrial materials, said compositions pertaining to the present invention, show controlling effects against micro-organisms which grow on the industrial materials and cause deterioration of their base materials. Such microorganisms may include, for example, paper/pulp-deteriorating microorganisms including slime-forming microorganisms, such as *Aspergillus sp., Trichoderma sp., Penicillium sp., Geotrichum sp., Chaetomium sp., Cadophora sp., Ceratostomella sp., Cladosporium sp., Corticium sp., Lentinus sp., Lezites sp., Phoma sp., Polysticus sp., Pullularia sp., Stereum sp., Trichosporium sp., Aerobacter sp., Bacillus sp., Desulfovibrio sp., Pseudomonas sp., Flavobacterium sp.* and *Micrococcus sp.*; fibers-deteriorating microorganisms such as *Aspergillus sp., Penicillium sp., Chaetomium sp., Myrothecium sp., Curvularia sp., Gliomastix sp., Memnoniella sp., Sarcopodium sp., Stachybotrys sp., Stemphylium sp., Zygorhynchus sp., Bacillus sp.* and *Staphylococcus sp.*; lumber-deteriorating microorganisms such as *Tyromyces palustris, Coriolus versicolor, Aspergillus sp., Penicillium sp., Rhizopus sp., Aureobasidium sp., Gliocladium sp., Cladosporium sp., Chaetomium sp.* and *Trichoderma sp.*; leather-deteriorating microorganisms such as *Aspergillus sp., Penicillium sp., Chaetomium sp.,*

*Cladosporium sp., Mucor sp., Paecilomyces sp., Pilobus sp., Pullularia sp., Trichosporon sp.* and *Tricothecium sp.*; rubber/plastics-deteriorating microorganisms such as *Aspergillus sp., Penicillium sp., Rhizopus sp., Trichoderma sp., Chaetomium sp., Myrothecium sp., Streptomyces sp., Pseudomonus sp., Bacillus sp., Micrococcus sp., Serratia sp., Margarinomyces sp.* and *Monascus sp.*; paint-deteriorating microorganisms such as *Aspergillus sp., Penicillium sp., Cladosporium sp., Aureobasidium sp., Gliocladium sp., Botryodiplodia sp., Macrosporium sp., Monilia sp., Phoma sp., Pullularia sp., Sporotrichum sp., Trichoderma sp., Bacillus sp., Proteus sp., Pseudomonas sp.* and *Serratia sp.*

The biocidal compositions for industrial materials, said compositions pertaining to the present invention, can each be formulated by dissolving or dispersing an effective amount of the compound represented by the formula (I) in a suitable liquid vehicle or mixing it with a solid vehicle and optionally adding an emulsifier, dispersant, spreading agent, penetrant, wetting agent, stabilizer and/or the like. One or more of other biocides, insecticides, deterioration inhibitors and the like may also be incorporated.

Any liquid may be used as a liquid vehicle so long as it does not react with the effective ingredient. It is possible to use, for example, water, an alcohol such as methyl alcohol, ethyl alcohol, ethylene glycol or cellosolve, a ketone such as acetone or methyl ethyl ketone, an ether such as dimethyl ether, diethyl ether, dioxane or tetrahydrofuran, an aromatic hydrocarbon such as benzene, toluene, xylene or methylnaphthalene, an aliphatic hydrocarbon such as gasoline, kerosine, lamp oil, stove oil, furnace oil, machine oil or fuel oil, an acid amide such as dimethylformamide or N-methylpyrrolidone, a halogenated hydrocarbon such as chloroform or carbon tetrachloride, an ester such as ethyl acetate or the glycerin ester of a fatty acid, a nitrile such as acetonitrile, dimethylsulfoxide, or the like. As a solid vehicle on the other hand, it is possible to use fine particulate or granular material such as clay, kaolin clay, bentonite, acid clay, pyrophyllite, talc, diatomaceous earth, calcite, urea or ammonium sulfate. As an emulsifier or dispersant, it is possible to use a surfactant such as a soap, alkyl sulfonate, alkyl arylsulfonate, dialkyl sulfosuccinate, quaternary ammonium salt, oxyalkylamine, fatty acid ester, polyalkylene-oxide-type surfactant or anhydrosorbitol-type surfactant.

Upon formulation of the azole derivative of the formula (I) as an effective ingredient into a biocidal composition according to this invention, it is generally suitable to add it to give a concentration of 0.1–99.9 wt.% although its content may vary depending on the preparation form and application purpose of the biocidal composition.

In the present invention, a biocidally-effective amount of the azole derivative of the formula (I) can be applied in a preparation form, for example, as a wettable powder, dust, granules, paste, suspension or spray to an industrial material. The application to the industrial material can be effected, for example, by spraying or coating the surface of paper, pulp, fibers, lumber, leather, rubber product, synthetic resin product or coating. The biocidally-effective amount may be generally 0.005–5 wt.% or preferably 0.01–1 wt.%, both, based on an industrial material to be treated.

EXAMPLES

Preparation Example

Preparation of a typical azole derivative of the formula (I) will hereinafter be described. It should however be noted that the other azole derivatives of the formula (I) can also be prepared likewise.

Preparation of
2-(4-chlorobenzyl)-2,5,5-trimethyl-1-(1H-1,2,4-triazol-1-ylmethyl)-1-cyclopentanol (Compound No. 111 in Table 1)

Anhydrous dimethylformamide (3 ml) was added with 230 mg of sodium hydride and further with 390 mg of 1H-1,2,4-triazole. The resultant mixture was stirred at room temperature until foaming subsided. The resulting solution was added with 2 ml of an anhydrous dimethylformamide solution which contained 1.0 g of 4-(4-chlorobenzyl)-4,7,7-trimethyl-1-oxaspiro[[2.4]heptane, followed by stirring at 120° C. for 24 hours. After allowing the thus-obtained reaction mixture to cool down, it was poured into ice water and then extracted with methylene chloride to obtain an organic layer. After washing the organic layer with aqueous saline solution, it was dried over anhydrous sodium sulfate, and the solvent was thereafter distilled off under reduced pressure. The thus-obtained residue was subjected to and purified by chromatography on a silica gel column (eluent: ethyl acetate). It was then recrystallized from n-hexane-ethyl acetate so that 1.06 g of the target compound was obtained.

By the way, the raw material,4-(4-chlorobenzyl)-4,7,7-trimethyl-1-oxaspiro[2.4]heptane, was obtained in the following manner.

2-(4-Chlorobenzyl)-2,5,5-trimethyl-1-methylenecyclopentane (6.1 g) was dissolved in 60 ml of chloroform, followed by the addition of 8.5 g of m-chloroperbenzoic acid. The resultant mixture was stirred for 5 hours under ice cooling. Calcium hydroxide (4.0 g) was added, followed by stirring at room temperature for 30 minutes. A solid thus precipitated was filtered off. From the chloroform layer as the filtrate, chloroform was distilled off under reduced pressure to obtain a colorless oily substance. The substance was subjected to and purified by chromatography on a silica gel column (eluent: 6:1 mixed solvent of n-hexane and methylene chloride), thereby obtaining 2.0 g of 4-(4-chlorobenzyl)-4,7,7-trimethyl-1-oxaspiro[2.4]heptane used in the above Preparation Example.

Biocidal Compositions and Tests

The present invention will hereinafter be described further by the following exemplary biocidal compositions and tests.

Composition 1:

A dust was obtained by grinding and mixing wt.% of an invention compound (Compound No. 87), 9 wt.% of kaolin clay and 10 wt.% of talc.

Composition 2:

A wettable powder was obtained by grinding and mixing 25 wt.% of an invention compound (Compound No. 2 wt.% of sodium ligninsulfonate, 2 wt.% of sodium lauryl sulfate and 71 wt.% of clay.

Test 1

Each test compound according to this invention was added to a modified Mueller-Hinton culture medium (product of Nissui Seiyaku Kabushiki Kaisha) to give a predetermined concentration. The resultant culture medium was poured into Petri dishes and was caused to coagulate. They were inoculated with three kinds of noxious microorganisms (*Staphylococcus sp.*, *Bacillus sp.* and *Micrococcus sp.*) respectively, followed by incubation at 37° C. Depending on whether those microorganisms had grown or not on the following day, the minimum inhibitory concentrations of the invention compound for the respective noxious microorganisms were determined. Based on the minimum inhibitory concentrations thus obtained, 5-stage ranking was conducted in accordance with the following system:

Minimum Inhibitory Concentration 1 at least 100 ppm
2 at least 50 ppm but lower than 100 ppm
3 at least 12.5 ppm but lower than 50 ppm
4 at least 3.13 ppm but lower than 12.5 ppm
5 lower than 3.13 ppm

TABLE 2

| Sample compound (No. in Table 1) | Test microorganism | | |
|---|---|---|---|
| | S. sp. | B. sp. | M. sp. |
| 1 | 2 | 3 | 3 |
| 3 | 2 | 3 | 5 |
| 4 | 2 | 3 | 5 |
| 5 | 2 | 3 | 4 |
| 6 | 2 | 2 | 3 |
| 7 | 3 | 3 | 4 |
| 8 | 2 | 2 | 4 |
| 9 | 1 | 2 | 3 |
| 10 | 1 | 2 | 2 |
| 11 | 1 | 3 | 5 |
| 12 | 1 | 3 | 4 |
| 13 | 3 | 3 | 4 |
| 14 | 3 | 3 | 4 |
| 16 | 2 | 2 | 3 |
| 17 | 2 | 3 | 4 |
| 19 | 2 | 1 | 2 |
| 23 | 1 | 2 | 3 |
| 24 | 2 | 2 | 3 |
| 25 | 2 | 3 | 4 |
| 26 | 2 | 3 | 4 |
| 27 | 2 | 3 | 3 |
| 28 | 3 | 4 | 5 |
| 29 | 2 | 2 | 3 |
| 30 | 2 | 2 | 4 |
| 31 | 2 | 2 | 2 |
| 32 | 3 | 2 | 3 |
| 34 | 3 | 3 | 4 |
| 36 | 4 | 5 | 5 |
| 37 | 3 | 3 | 4 |
| 38 | 3 | 3 | 4 |
| 39 | 3 | 4 | 5 |
| 40 | 3 | 3 | 4 |
| 41 | 4 | 5 | 5 |
| 42 | 1 | 2 | 2 |
| 43 | 1 | 3 | 4 |
| 44 | 3 | 3 | 3 |
| 45 | 3 | 4 | 5 |
| 47 | 4 | 5 | 5 |
| 48 | 3 | 3 | 4 |
| 49 | 4 | 4 | 5 |
| 50 | 3 | 3 | 4 |
| 51 | 4 | 3 | 4 |
| 52 | 4 | 4 | 5 |
| 53 | 2 | 1 | 2 |
| 54 | 4 | 4 | 4 |
| 55 | 3 | 3 | 4 |
| 56 | 3 | 3 | 4 |

TABLE 2-continued

| Sample compound (No. in Table 1) | Test microorganism | | |
|---|---|---|---|
| | S. sp. | B. sp. | M. sp. |
| 57 | 3 | 4 | 5 |
| 58 | 4 | 4 | 5 |
| 59 | 3 | 4 | 5 |
| 60 | 3 | 4 | 4 |
| 61 | 3 | 4 | 5 |
| 62 | 3 | 2 | 3 |
| 63 | 3 | 2 | 4 |
| 64 | 3 | 3 | 5 |
| 65 | 3 | 3 | 4 |
| 66 | 4 | 3 | 5 |
| 67 | 3 | 3 | 5 |
| 68 | 3 | 2 | 4 |
| 69 | 3 | 3 | 4 |
| 70 | 3 | 3 | 5 |
| 71 | 4 | 3 | 4 |
| 75 | 3 | 3 | 4 |
| 76 | 3 | 4 | 4 |
| 78 | 1 | 1 | 3 |
| 80 | 1 | 2 | 3 |
| 81 | 1 | 3 | 3 |
| 82 | 3 | 3 | 5 |
| 84 | 1 | 2 | 3 |
| 86 | 1 | 3 | 4 |
| 90 | 3 | 4 | 5 |
| 92 | 1 | 2 | 3 |
| 94 | 1 | 2 | 3 |
| 96 | 1 | 2 | 3 |
| 98 | 1 | 2 | 4 |
| 101 | 1 | 3 | 4 |
| 103 | 2 | 3 | 4 |
| 104 | 1 | 1 | 3 |
| 105 | 2 | 3 | 4 |
| 107 | 1 | 3 | 5 |

The abbreviation in Table 2 shows each of the following microorganisms:
S. sp.; *Staphylococcus sp.*
B. sp.; *Bacillus sp.*
M. sp.; *Micrococcus sp.*

Test 2

Each test compound according to this invention was added to a potato-sucrose-agar culture medium to give 100 ppm. The resultant culture medium was poured into Petri dishes and was caused to coagulate. They were inoculated with seven kinds of noxious microorganisms (*Aspergillus niger*, *Aspergillus terreus*, *Aureobasidium pullulans*, *Rhizopus stolonifer*, *Penicillium citrinum*, *Penicillium funiculosum* and *Chaetomium globosum*) respectively, followed by incubation at 28° C. for 7 days. Hyphae elongation inhibitory rates (%) were determined respectively in accordance with the below-described equation. Based on the hyphae elongation inhibitory rates, the test results were ranked in four stages by the following ranking system. The results are shown in Table 3.

$$\text{Hyphae elongation inhibitory rate, \%} = \frac{\text{Hyphae elongation in non-treated group, mm} - \text{Hyphae elongation in treated group, mm}}{\text{Hyphae elongation in non-treated group, mm}} \times 100$$

Ranking System

Hyphae Elongation Inhibitory Rate, %

1 at least 0% but smaller than 25%
2 at least 25% but smaller than 50%
3 at least 50% but smaller than 75%
4 at least 75% and up to 100%

TABLE 3

| Sample compound (No. in Table 1) | Asp. t. | Asp. n. | Aur. p. | Rhi. s. | Pen. c. | Pen. f. | Chae. g. |
|---|---|---|---|---|---|---|---|
| 1 | 4 | 4 | 4 | 4 | 4 | 4 | 4 |
| 2 | 4 | 4 | 4 | 4 | 2 | 4 | 4 |
| 3 | 4 | 4 | 4 | 4 | 4 | 4 | 4 |
| 4 | 4 | 4 | 4 | 4 | 4 | 4 | 4 |
| 5 | 4 | 4 | 4 | 4 | 4 | 4 | 4 |
| 6 | 4 | 4 | 4 | 4 | 2 | 4 | 4 |
| 7 | 4 | 4 | 4 | 4 | 4 | 4 | 4 |
| 8 | 4 | 4 | 4 | 4 | 4 | 4 | 4 |
| 9 | 4 | 4 | 4 | 4 | 4 | 4 | 4 |
| 10 | 4 | 4 | 4 | 4 | 1 | 4 | 4 |
| 11 | 4 | 4 | 4 | 4 | 4 | 4 | 4 |
| 12 | 4 | 4 | 4 | 4 | 4 | 4 | 4 |
| 13 | 4 | 4 | 4 | 4 | 2 | 4 | 4 |
| 14 | 2 | 4 | 4 | 4 | 2 | 4 | 4 |
| 19 | 4 | 4 | 4 | 4 | 2 | 4 | 4 |
| 20 | 4 | 4 | 4 | 4 | 4 | 4 | 4 |
| 21 | 4 | 4 | 4 | 4 | 4 | 4 | 4 |
| 22 | 4 | 4 | 4 | 4 | 4 | 4 | 4 |
| 23 | 4 | 4 | 4 | 4 | 4 | 4 | 4 |
| 24 | 4 | 4 | 4 | 4 | 2 | 4 | 4 |
| 25 | 4 | 4 | 4 | 4 | 4 | 4 | 4 |
| 26 | 4 | 4 | 4 | 4 | 4 | 4 | 4 |
| 27 | 4 | 4 | 4 | 4 | 4 | 4 | 4 |
| 28 | 4 | 4 | 4 | 4 | 4 | 4 | 4 |
| 29 | 4 | 4 | 4 | 4 | 4 | 4 | 4 |
| 30 | 4 | 4 | 4 | 4 | 4 | 4 | 4 |
| 31 | 4 | 4 | 4 | 4 | 4 | 4 | 4 |
| 32 | 4 | 4 | 4 | 4 | 4 | 4 | 4 |
| 33 | 4 | 4 | 4 | 4 | 4 | 4 | 4 |
| 34 | 4 | 4 | 4 | 4 | 4 | 4 | 4 |
| 35 | 4 | 4 | 4 | 4 | 4 | 4 | 4 |
| 36 | 4 | 4 | 4 | 4 | 4 | 4 | 4 |
| 37 | 4 | 4 | 4 | 4 | 4 | 4 | 4 |
| 38 | 4 | 4 | 4 | 4 | 4 | 4 | 4 |
| 39 | 4 | 4 | 4 | 4 | 4 | 4 | 4 |
| 40 | 1 | 4 | 4 | 4 | 4 | 4 | 4 |
| 41 | 4 | 4 | 4 | 4 | 4 | 4 | 4 |
| 42 | 4 | 4 | 4 | 4 | 4 | 4 | 4 |
| 43 | 4 | 4 | 4 | 4 | 4 | 4 | 4 |
| 44 | 4 | 4 | 4 | 4 | 4 | 4 | 4 |
| 45 | 4 | 4 | 4 | 4 | 4 | 4 | 4 |
| 46 | 2 | 4 | 1 | 1 | 4 | 1 | 4 |
| 47 | 4 | 4 | 1 | 1 | 4 | 4 | 4 |
| 48 | 1 | 4 | 4 | 3 | 2 | 1 | 4 |
| 49 | 4 | 4 | 4 | 4 | 4 | 4 | 4 |
| 50 | 4 | 4 | 4 | 4 | 4 | 4 | 4 |
| 51 | 4 | 4 | 4 | 4 | 4 | 4 | 4 |
| 52 | 4 | 4 | 4 | 4 | 4 | 4 | 4 |
| 53 | 4 | 4 | 4 | 4 | 4 | 4 | 4 |
| 54 | 4 | 4 | 4 | 4 | 4 | 3 | 4 |
| 55 | 4 | 4 | 4 | 3 | 4 | 1 | 4 |
| 56 | 2 | 3 | 4 | 3 | 2 | 2 | 4 |
| 57 | 4 | 4 | 1 | 1 | 4 | 4 | 4 |
| 58 | 4 | 4 | 4 | 4 | 4 | 4 | 4 |
| 59 | 4 | 4 | 4 | 4 | 4 | 4 | 4 |
| 60 | 2 | 3 | 3 | 1 | 2 | 1 | 4 |
| 61 | 4 | 4 | 4 | 1 | 4 | 2 | 4 |
| 63 | 4 | 4 | 4 | 4 | 4 | 4 | 4 |
| 64 | 4 | 4 | 4 | 4 | 4 | 4 | 4 |
| 66 | 4 | 4 | 4 | 4 | 4 | 4 | 4 |
| 67 | 4 | 4 | 4 | 4 | 4 | 4 | 4 |
| 68 | 2 | 3 | 4 | 3 | 2 | 1 | 4 |
| 69 | 4 | 4 | 4 | 4 | 4 | 3 | 4 |
| 70 | 4 | 4 | 4 | 4 | 4 | 4 | 4 |
| 71 | 4 | 4 | 4 | 4 | 4 | 4 | 4 |
| 75 | 1 | 2 | 3 | 1 | 1 | 2 | 4 |
| 76 | 4 | 4 | 4 | 4 | 4 | 4 | 4 |
| 77 | 2 | 4 | 4 | 1 | 1 | 2 | 4 |
| 78 | 4 | 4 | 1 | 1 | 3 | 4 | 4 |
| 79 | 4 | 4 | 4 | 1 | 3 | 3 | 4 |
| 80 | 4 | 4 | 4 | 4 | 4 | 3 | 4 |
| 81 | 1 | 3 | 4 | 1 | 3 | 1 | 4 |
| 82 | 1 | 4 | 1 | 1 | 4 | 1 | 4 |
| 84 | 1 | 4 | 4 | 1 | 2 | 3 | 4 |
| 85 | 4 | 4 | 1 | 1 | 4 | 2 | 4 |
| 86 | 4 | 4 | 2 | 1 | 4 | 4 | 4 |
| 87 | 4 | 4 | 4 | 4 | 4 | 4 | 4 |
| 88 | 4 | 4 | 4 | 4 | 4 | 4 | 4 |
| 89 | 1 | 4 | 4 | 4 | 2 | 4 | 4 |
| 90 | 4 | 4 | 4 | 4 | 4 | 4 | 4 |

TABLE 3-continued

| Sample compound (No. in Table 1) | Test microorganism | | | | | | |
|---|---|---|---|---|---|---|---|
| | Asp. t. | Asp. n. | Aur. p. | Rhi. s. | Pen. c. | Pen. f. | Chae. g. |
| 91 | 2 | 4 | 4 | 4 | 1 | 2 | 4 |
| 92 | 4 | 4 | 1 | 4 | 4 | 4 | 4 |
| 94 | 1 | 4 | 1 | 1 | 2 | 3 | 4 |
| 96 | 3 | 4 | 4 | 1 | 2 | 2 | 4 |
| 97 | 4 | 4 | 4 | 4 | 3 | 3 | 4 |
| 98 | 4 | 4 | 1 | 1 | 4 | 4 | 4 |
| 99 | 1 | 4 | 4 | 4 | 1 | 1 | 4 |
| 101 | 4 | 4 | 4 | 1 | 4 | 2 | 4 |
| 102 | 2 | 4 | 4 | 4 | 2 | 4 | 4 |
| 103 | 4 | 4 | 4 | 4 | 4 | 4 | 4 |
| 104 | 4 | 4 | 4 | 4 | 4 | 4 | 4 |
| 105 | 4 | 4 | 4 | 4 | 4 | 4 | 4 |
| 106 | 1 | 4 | 1 | 1 | 4 | 2 | 4 |
| 107 | 4 | 4 | 4 | 1 | 4 | 4 | 4 |
| 109 | 2 | 4 | 4 | 1 | 1 | 1 | 4 |
| 111 | 4 | 4 | 4 | 4 | 4 | 4 | 4 |
| 112 | 1 | 4 | 4 | 1 | 1 | 1 | 4 |
| 113 | 4 | 4 | 4 | 4 | 4 | 4 | 4 |
| 114 | 4 | 4 | 4 | 4 | 4 | 4 | 4 |

The abbreviation in Table 3 shows each of the following microorganisms:
Asp. t.; *Aspergillus terreus*
Asp. n.; *Aspergillus niger*
Aur. p.; *Aureobasidium pullulans*
Rhi. s.; *Rhizopus stolonifer*
Pen. c.; *Penicillium citrinum*
Pen. f.; *Penicillium funiculosum*
Chae. g.; *Chaetomium globosum*

We claim:

1. A treated industrial material resistant to deterioration by bacteria noxious to the untreated industrial material,
    wherein the industrial material is selected from the group consisting of paper, pulp, fibers, leather, rubber and synthetic resins;
    said industrial material having been treated with a triazole derivative in an amount which renders said industrial material bactericidally resistant to deterioration by said bacteria, said triazole derivative being a compound represented by the following formula (I):

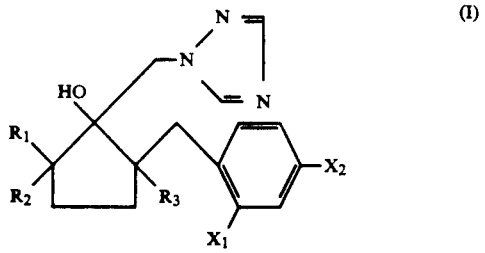

wherein
    $X_1$ and $X_2$ individually are selected from the group consisting of a hydrogen atom, a halogen atom, and $C_1$–$C_4$ alkyl, phenyl and cyano groups, $R_1$ and $R_2$ individually are selected from the group consisting of a hydrogen atom and $C_1$–$C_5$ alkyl groups, and $R_3$ is selected from the group consisting of a hydrogen atom and $C_1$–$C_3$ alkyl groups; and
wherein
    (i) when $R_1$, $R_2$, $R_3$ and $X_1$ are hydrogen atoms, $X_2$ is selected from the group consisting of cyano, phenyl, fluorine, chlorine and bromine;
    (ii) when $R_1$, $R_2$ and $R_3$ are hydrogen atoms and $X_1$ is a fluorine atom, $X_2$ is selected from the group consisting of fluorine and chlorine;
    (iii) when $R_1$, $R_2$ and $R_3$ are hydrogen atoms and $X_1$ is a chlorine atom, $X_2$ is a chlorine atom;
    (iv) when $R_1$ and $R_2$ are individually selected from the group consisting of a hydrogen atom and $C_1$–$C_5$ alkyl groups, $R_3$ is a hydrogen atom, and $X_1$ is a hydrogen atom, $X_2$ is selected from the group consisting of $C_1$–$C_4$ alkyl and phenyl groups, fluorine, chlorine and bromine, provided that one of $R_1$ and $R_2$ is not a hydrogen atom;
    (v) when $R_1$ and $R_2$ are individually selected from the group consisting of a hydrogen atom and $C_1$–$C_5$ alkyl groups, $R_3$ is a hydrogen atom and $X_1$ is chlorine or fluorine, $X_2$ is chlorine provided that one of $R_1$ and $R_2$ is not a hydrogen atom; and
    (vi) when $R_1$ and $R_2$ are individually a $C_1$–$C_5$ alkyl group and $R_3$ is a $C_1$–$C_3$ alkyl group, $X_1$ is a hydrogen atom and $X_2$ is a chlorine atom.

2. The treated industrial material as defined in claim 1, wherein said bactericidally effective amount ranges from 0.005 to 5 weight percent, based on the untreated industrial material.

3. The treated industrial material as defined in claim 1, wherein said bactericidally effective amount ranges from 0.01 to 1 weight percent, based on the untreated industrial material.

4. A method for preventing bacterial deterioration of an industrial material,
    wherein the industrial material is selected from the group consisting of paper, pulp, fibers, leather, rubber and synthetic resins;
    which comprises applying to said industrial material a bacterial composition, said bacterial composition comprising a vehicle and a triazole derivative, said bacterial composition being applied to said industrial material in an amount which is bactericidally effective against said bacteria causing said deterioration, said triazole derivative being of the following formula (I):

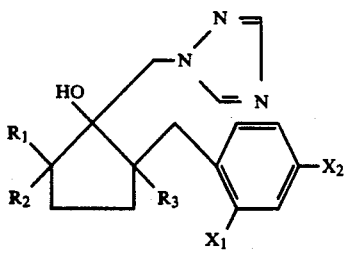

(I)

wherein $X_1$ and $X_2$ individually are selected from the group consisting of a hydrogen atom, a halogen atom, and $C_1$-$C_4$ alkyl, phenyl and cyano groups, $R_1$ and $R_2$ individually are selected from the group consisting of a hydrogen atom and $C_1$-$C_5$ alkyl groups, and $R_3$ is selected from the group consisting of a hydrogen atom and $C_1$-$C_3$ alkyl groups; and wherein (i) when $R_1$, $R_2$, $R_3$ and $X_1$ are hydrogen atoms, $X_2$ is selected from the group consisting of cyano, phenyl, fluorine, chlorine and bromine;

(ii) when $R_1$, $R_2$ and $R_3$ are hydrogen atoms and $X_1$ is a fluorine atom, $X_2$ is selected from the group consisting of fluorine and chlorine;

(iii) when $R_1$, $R_2$ and $R_3$ are hydrogen atoms and $X_1$ is a chlorine atom, $X_2$ is a chlorine atom;

(iv) when $R_1$ and $R_2$ are individually selected from the group consisting of a hydrogen atom and $C_1$-$C_5$ alkyl groups, $R_3$ is a hydrogen atom and $X_1$ is a hydrogen atom, $X_2$ is selected from the group consisting of $C_1$-$C_4$ alkyl and phenyl groups, fluorine, chlorine and bromine, provided that one of $R_1$ and $R_2$ is not a hydrogen atom;

(v) when $R_1$ and $R_2$ are individually selected from the group consisting of hydrogen atom and $C_1$-$C_5$ alkyl groups, $R_3$ is a hydrogen atom and $X_1$ is chlorine or fluorine, $X_2$ is chlorine provided that one of $R_1$ and $R_2$ is not a hydrogen atom; and (vi) when $R_1$ and $R_2$ are individually a $C_1$-$C_5$ alkyl group and $R_3$ is a $C_1$-$C_3$ alkyl group, $X_1$ is a hydrogen atom and $X_2$ is a chlorine atom.

5. The method as defined in claim 4, wherein said bactericidally effective amount ranges from 0.005-5 weight percent based on the untreated industrial material.

6. The method as defined in claim 4, wherein said bactericidally effective amount ranges from 0.01 to 1 weight percent based on the untreated industrial material.

* * * * *

UNITED STATES PATENT AND TRADEMARK OFFICE
CERTIFICATE OF CORRECTION

PATENT NO. : 5,292,764

DATED : March 8, 1994

INVENTOR(S) : Masato ARAHIRA et al

It is certified that error appears in the above-identified patent and that said Letters Patent is hereby corrected as shown below:

Column 4, lines 1-19, please delete the chemical formulas and insert the following therefor:

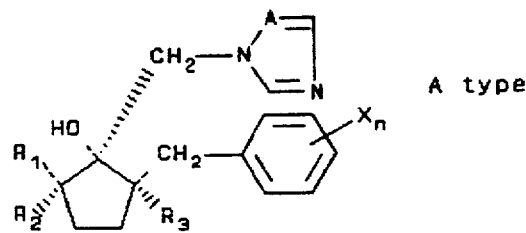

A type

UNITED STATES PATENT AND TRADEMARK OFFICE
CERTIFICATE OF CORRECTION

PATENT NO. : 5,292,764
DATED : March 8, 1994
INVENTOR(S) : Masato ARAHIRA et al

It is certified that error appears in the above-indentified patent and that said Letters Patent is hereby corrected as shown below:

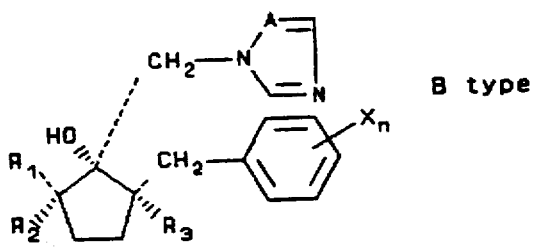

Signed and Sealed this

Fifteenth Day of November, 1994

Attest:

BRUCE LEHMAN

Attesting Officer        Commissioner of Patents and Trademarks